(12) United States Patent
Welch et al.

(10) Patent No.: US 8,193,404 B2
(45) Date of Patent: Jun. 5, 2012

(54) USE OF A DIRECT HEATING DEVICE WITH A REHEATER IN A DEHYDROGENATION UNIT

(75) Inventors: Vincent A. Welch, Medway, MA (US); Slawomir A. Oleksy, Billerica, MA (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 13/301,852

(22) Filed: Nov. 22, 2011

(65) Prior Publication Data

US 2012/0078025 A1 Mar. 29, 2012

Related U.S. Application Data

(63) Continuation of application No. 12/422,880, filed on Apr. 13, 2009, now Pat. No. 8,084,660.

(60) Provisional application No. 61/124,619, filed on Apr. 18, 2008.

(51) Int. Cl.
*C07C 5/327* (2006.01)
*C07C 5/333* (2006.01)

(52) U.S. Cl. .................. 585/440; 585/889; 585/910

(58) Field of Classification Search .............. 585/440, 585/889, 910
See application file for complete search history.

(56) References Cited

U.S. PATENT DOCUMENTS 6,392,113 B1 * 5/2002 Gartside ............... 585/654
* cited by examiner

*Primary Examiner* — Thuan Dinh Dang

(57) ABSTRACT

Methods and processes for increasing the efficiency and/or expanding the capacity of a dehydrogenation unit by use of at least one direct heating unit are described.

7 Claims, 5 Drawing Sheets

USE OF A DIRECT HEATING DEVICE WITH A REHEATER IN A DEHYDROGENATION UNIT

CROSS-REFERENCE TO RELATED APPLICATIONS

This application is a continuation of U.S. application Ser. No. 12/422,880 filed on Apr. 13, 2009, now U.S. Pat. No. 8,084,660, which claims the benefit of U.S. Provisional Application No. 61/124,619, filed Apr. 18, 2008.

FIELD

This invention generally relates to the dehydrogenation of aromatic compounds and more particularly discloses methods and apparatus for the dehydrogenation of ethylbenzene into styrene monomer.

BACKGROUND

Various vinyl aromatic compounds can be prepared by the catalytic dehydrogenation of corresponding $C_2$ or $C_3$ alkyl aromatic compounds. Such reactions include the catalytic dehydrogenation of monoalkyl or polyalkyl aromatics, such as ethylbenzene and diethylbenzene or the dehydrogenation of alkyl substituted polynuclear aromatic compounds, such as ethylnaphthalene. Perhaps the mostly widely used dehydrogenation process involves the dehydrogenation of ethylbenzene for the production of styrene. Analogous dehydrogenation reactions can be carried out employing $C_3$ alkyl aromatic compounds. Thus, n-propyl benzene can be dehydrogenated to produce beta methyl styrene, and cumene can be dehydrogenated to produce alpha methyl styrene. Other reactions include but are not limited to the dehydrogenation of ethyl toluene to produce vinyl toluene and the dehydrogenation of diethylbenzene to produce divinylbenzene.

It is well known in the art of styrene manufacture to react ethylbenzene (EB) in the presence of steam over a dehydrogenation catalyst such as iron oxide under dehydrogenation reaction conditions in order to strip hydrogen from the ethyl group on the benzene ring to form the styrene molecule. This may be done in a series of reactors, which are commonly termed EB dehydrogenation reactors. The reactors may be radial adiabatic type reactors. The dehydrogenation reactors generally are elongated, cylindrical, vertical structures of a size ranging in diameter from about five to about sixteen feet or more, and in length from about ten feet to about one hundred feet or more. The reactor may allow for input of the ethylbenzene gas at an inlet located in the center of the vertical reactor, whereupon the gas is flowed radially outward through an annular area, passing through an annular porous catalyst bed of iron oxide or other suitable dehydrogenation catalyst, and then passing through an outer annular area to exit the reactor shell. Conversely, the input of ethylbenzene gas may enter the reactor via the outer most annulus area, passing through the catalyst bed in the direction of the center of the reactor. Because the flow of ethylbenzene across the catalyst bed is in a radial direction, these reactors are sometimes identified as "radial" reactors.

In some embodiments of an EB dehydrogenation process there can be multiple radial adiabatic reactors arranged in series, with one or more ways of reheating between the reactors to add heat lost to the endothermic reaction. Each reactor may have a different selectivity catalyst from the catalyst of the other reactors. "Selectivity" in this instance is considered by one skilled in the art to mean the ability of the catalyst to selectively produce higher levels of the desirable styrene and lower levels of the undesirable toluene and benzene. "Activity" is considered to be the ability of the catalyst to convert a certain percentage of ethylbenzene to aromatics for each pass of feedstock over the catalyst at a specific temperature. An example of a conventional radial reactor can be found in U.S. Pat. No. 5,358,698 to Butler, et al.

Because of the adiabatic design of conventional EB dehydrogenation reactors and the endothermic nature of the dehydrogenation reaction, conventional EB dehydrogenation processes require the addition of heat to the process to drive the dehydrogenation reaction and achieve an economic per pass conversion of EB. This, in turn, necessitates the use of multiple reactors in order to provide opportunity to add heat during the process, which is accomplished by utilizing heaters or "reheaters" located between each of the serial reactors or between catalyst beds.

The additional heat into the process can be supplied, for example by indirect heat exchange with superheated steam, to the reheater located between two or more of the serial reactors. The superheated steam can have a temperature of approximately 1000° F. to 1650° F., for example. A limiting factor on the amount of heat that can be added to the process utilizing superheated steam may be the metallurgy of the reheater, the piping to the reheater, or the outlet piping of the heated reactants that may have a high temperature limit less than that of the superheated steam.

It is a continuing goal of the industry to heat hydrocarbon streams, especially reactant streams, uniformly and within relatively strict temperature limits to achieve the necessary temperatures, but also to avoid localized hot spots and consequential degradation of the hydrocarbon, such as to coking products.

For economic reasons it is desirable to lower the steam to hydrocarbon ratio of the process due to the costs incurred in generating and superheating steam. If hydrocarbon heating is no longer dependent upon the amount of steam needed to heat or reheat the process streams to and/or from reactors, more energy saving devices may be installed to lower the energy required to process the hydrocarbons. The desire to lower the steam to hydrocarbon ratio can be in conflict with the need to input heat into the process indirectly via a reheater. In view of the above, it would be beneficial to have a method of reducing the steam usage while also having the ability to independently add heat into the process.

SUMMARY OF THE INVENTION

The present invention generally relates to methods and processes utilizing at least one direct heating unit to increase the efficiency and/or expanding the capacity of a dehydrogenation unit. An embodiment is a method that includes providing at least one dehydrogenation reactor and a feed stream. At least one direct heating unit (DHU) is added to a new or existing dehydrogenation unit having a reheater, whereby the DHU and reheater are positioned before or after at least one reactor, and wherein the DHU and reheater are operated in a parallel arrangement with respect to each other. Between 0.5% and 85% of a reactor effluent from the reactor is diverted to the DHU for heating while the remainder of the reactor effluent is directed to the reheater for heating. The heated streams from the DHU and the reheater are directed to a subsequent reactor. There is an energy savings for operating the new or existing dehydrogenation unit with an added DHU as compared to operating a dehydrogenation unit with only a reheater and no added DHU.

The energy savings is a usage of 0.5% to 50% less energy when at least one DHU and at least one reheater are used to heat a process stream. A heated air stream can be supplied to the DHU. A cooled air stream can be supplied to the DHU. The reheater can utilize steam as a heat source.

Another embodiment is a method for increasing the efficiency and/or expanding the capacity of a new or existing dehydrogenation unit that includes providing at least one dehydrogenation reactor and a feed stream, adding at least one reheater and at least one direct heating unit (DHU) to the new or existing dehydrogenation unit. The DHU and reheater can be positioned before or after at least one reactor, and the DHU and reheater are in parallel arrangement with respect to each other. Between 0.5% and 85% of a reactor effluent from the reactor are diverted to the DHU for heating and the remainder of the reactor effluent goes to the reheater for heating. The heated streams from the DHU and the reheater to are fed to a subsequent reactor giving an energy savings for operating the new or existing dehydrogenation unit as compared to operating a dehydrogenation unit without an added DHU and added reheater.

DETAILED DESCRIPTION

The process of the subject invention generally comprises the addition of a Direct Heating Unit (DHU) in parallel to a reheater located between two or more of the serial EB dehydrogenation reactors.

Utilizing the ethylbenzene to styrene dehydrogenation reaction as a non-limiting example, generally the energy needed for the reaction to convert ethylbenzene to styrene is supplied by superheated steam (at about 1000° F. to 1650° F.) that is injected into a vertically mounted fixed bed catalytic reactor with vaporized ethylbenzene. The catalyst is typically iron oxide-based and contains one or more potassium compounds ($K_2O$ or $K_2CO_3$), which act as reaction promoters. Typically, 1-2 pounds of steam is required for each pound of ethylbenzene to ensure sufficiently high temperatures throughout the reactor. The superheated steam supplies the necessary reaction temperature of about 1000-1200° F. throughout the reactor. Ethylbenzene conversion is typically 60-70%. The system is generally operated under vacuum.

Because of the endothermic nature of the dehydrogenation reaction, conventional EB processes require the addition of heat to the process to maintain the dehydrogenation reaction at economic levels. This, in turn, necessitates the use of multiple reactors in order to provide opportunity to add heat during the process, which the prior art accomplished by utilizing heaters, commonly referred to as reheaters, located between each of the serial reactors.

Figure 1:
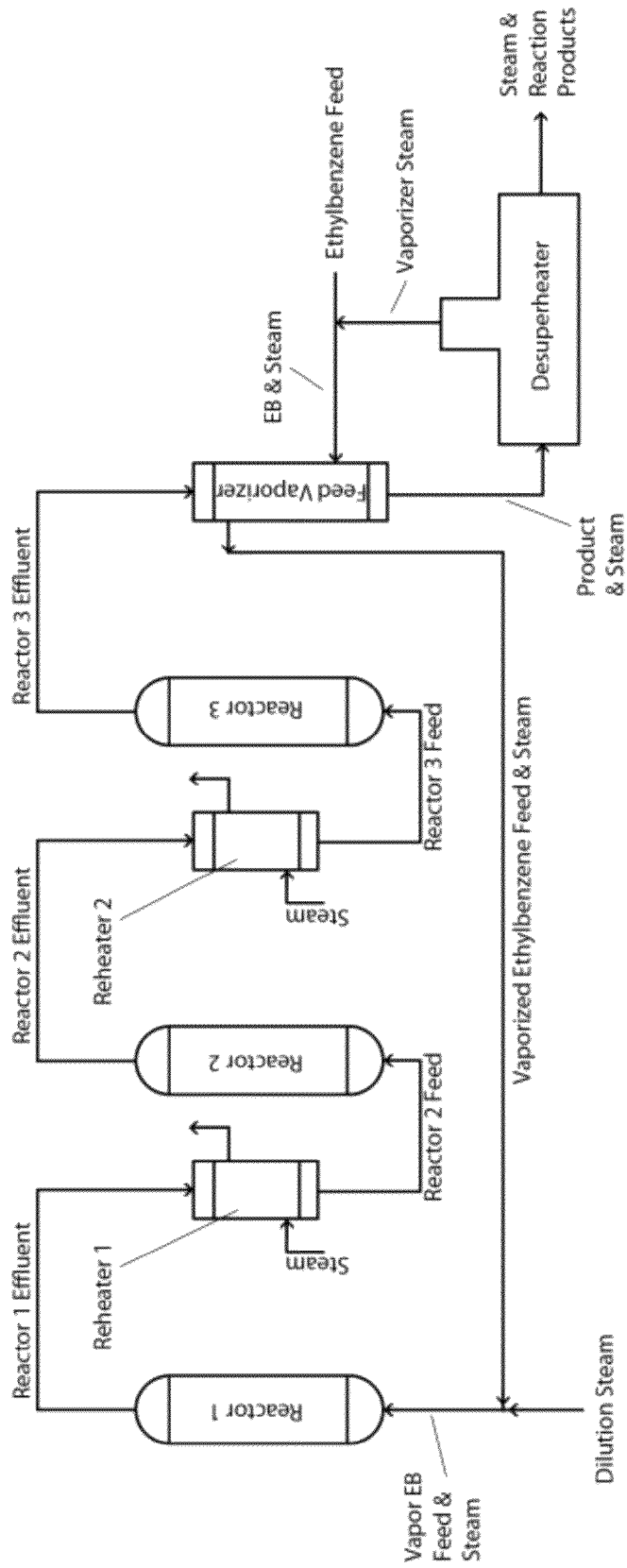
FIG. 1 illustrates a multiple reactor dehydrogenation system having typical steam reheaters located between the reactors.

FIG. 1 illustrates a conventional multiple reactor dehydrogenation system having a steam reheater located between the first and second reactor and between the second and third reactor.

Figure 2:
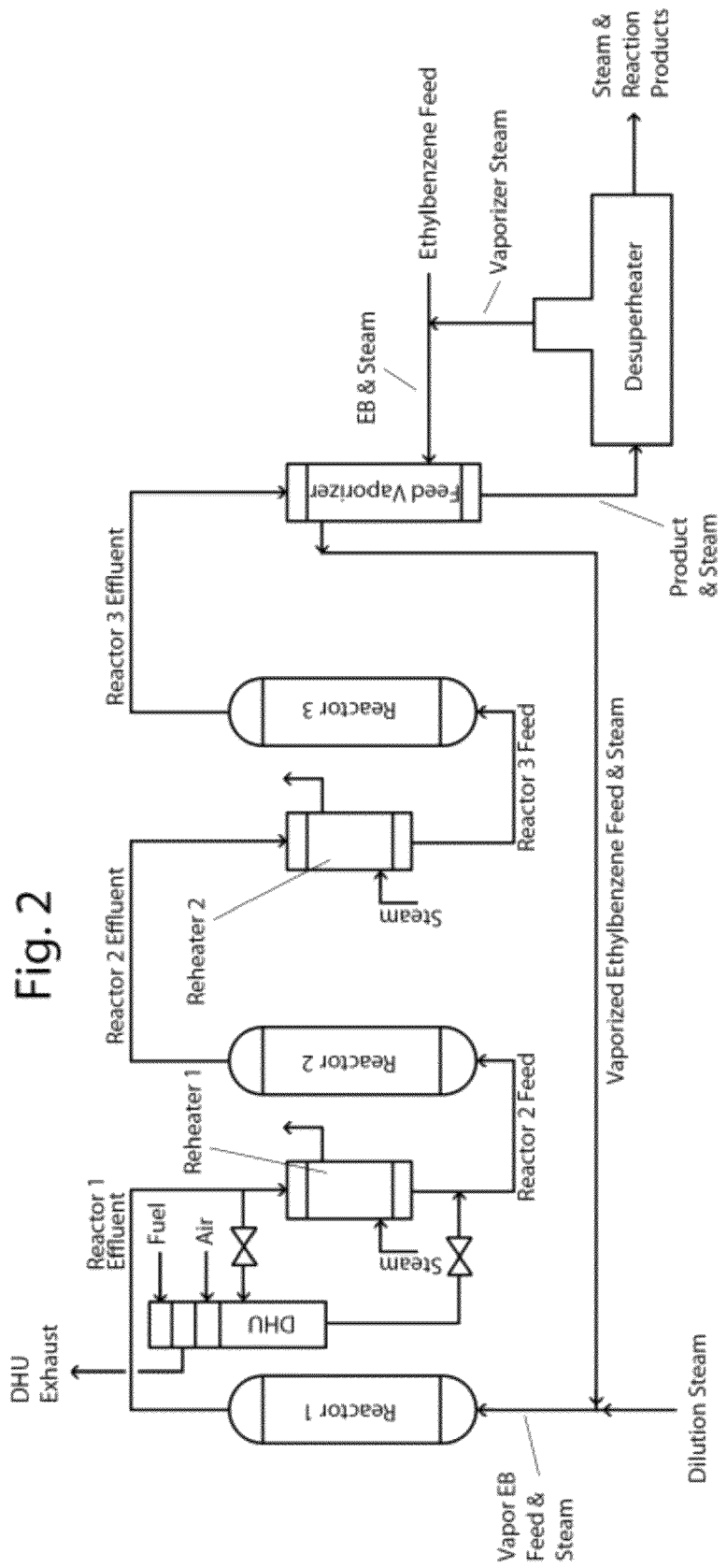
FIG. 2 illustrates an embodiment of a multiple reactor dehydrogenation system where a Direct Heating Unit (DHU) is added in parallel to the steam reheater located between the first and second reactor.

FIG. 2 illustrates an embodiment of the invention where a DHU is added and operated in parallel to the steam reheater located between the first and second reactor. Although not shown, a DHU can also be added in parallel with a steam reheater located between the second and third reactor (or any additional reactors), or prior to the first reactor.

Figure 3:
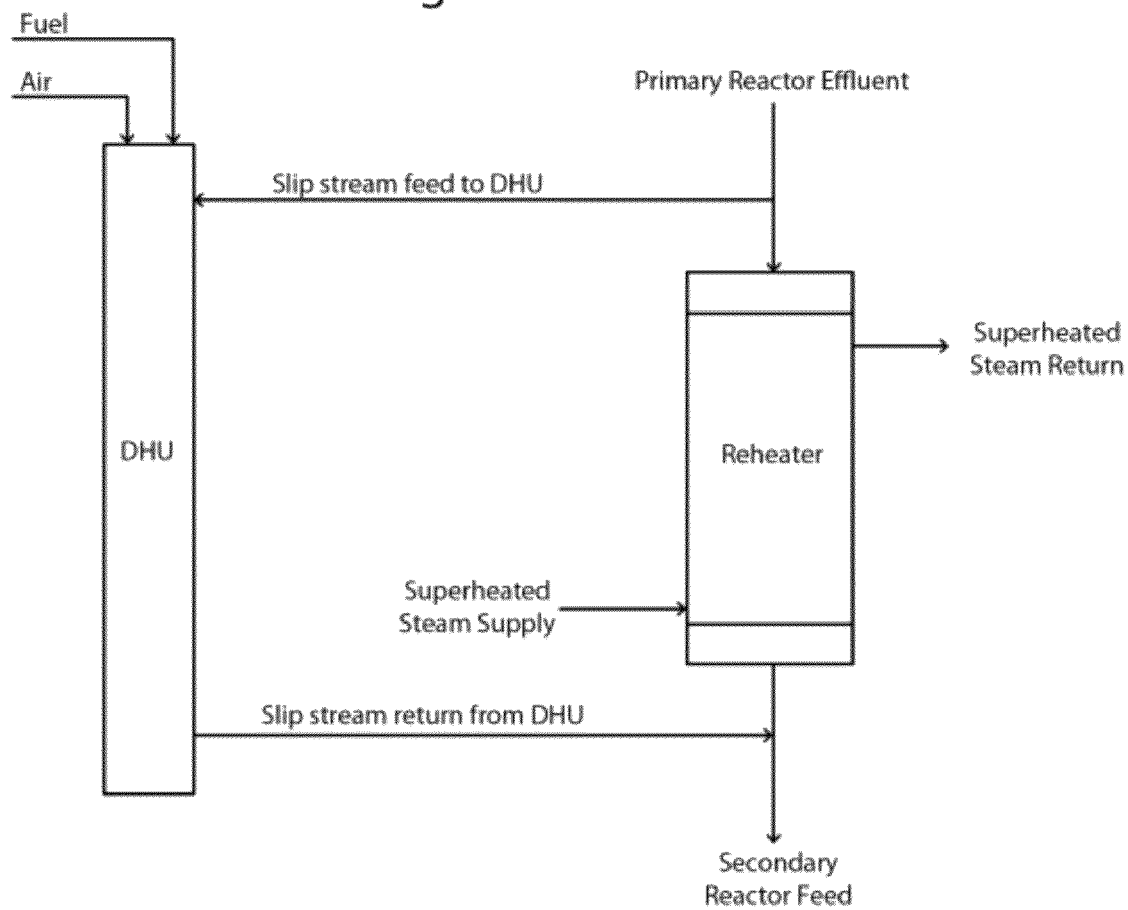
FIG. 3 illustrates an embodiment where a DHU is added in parallel to the steam reheater before a reactor.

FIG. 3 further illustrates an embodiment wherein a DHU is operated in parallel to a steam reheater. The combination of the reheater and the DHU in a parallel arrangement can enable the input of more heat into the reactant stream than can be accomplished by a reheater or a DHU alone.

The feed to the primary reactor is comprised of primarily of ethylbenzene and steam. The primary reactor effluent stream from the first reactor and can comprise a mixture of ethylbenzene, styrene, hydrogen, steam, and may contain small amounts of other components exiting the first stage (primary) reactor. A first portion of the primary reactor effluent enters the reheater where it is heated by cross exchange with a steam supply, which can be a superheated steam supply. A second portion of the primary reactor effluent enters the DHU rather than the reheater. The second portion of the primary reactor effluent is heated by heat exchange with the heat of combustion from the DHU. The first portion of the primary reactor effluent exiting the reheater combines with the second portion of the primary reactor effluent exiting the DHU to form the feed stream to the second stage (secondary) reactor.

The steam supply to the reheater can be superheated steam that is heated above the saturation temperature. The superheated steam return will be cooler steam as it has transferred heat to the process in the reheater.

The fuel stream to the DHU can be of any combustible fuel suitable for the application, such as for example natural gas, butane or hydrogen extracted from the dehydrogenation process. Other hydrocarbons extracted from the dehydrogenation process can also be used as a fuel source. Combinations of one or more of the fuel sources listed above, or other sources can also be used. Air is provided for the combustion of the fuel within the DHU. The air for the DHU can be heated or cooled as needed to increase the thermal efficiency of the DHU or to reduce emissions such as $CO_2$ or NOx.

Figure 4:
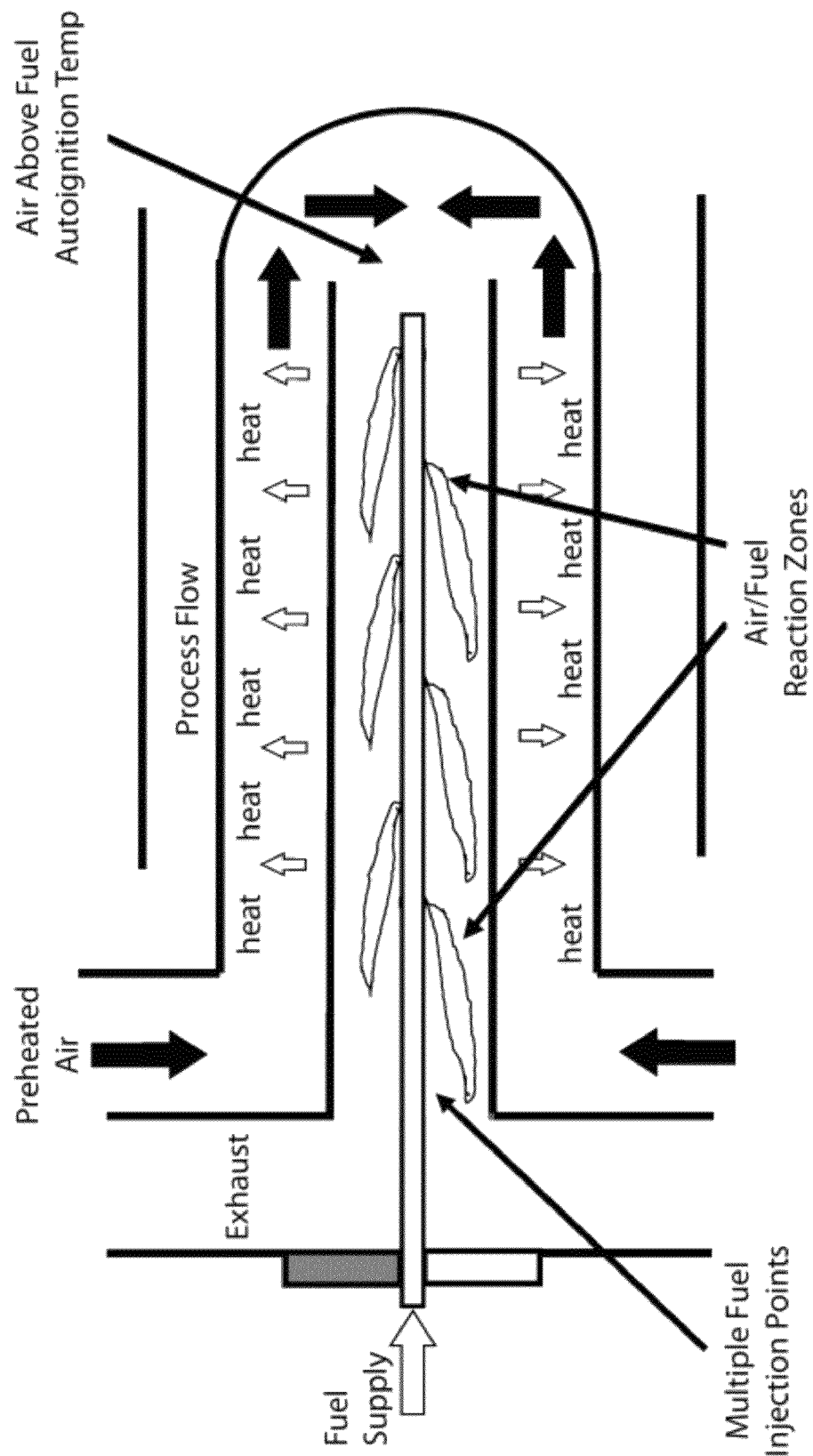
FIG. 4 is a schematic cross-sectional illustration of a non-limiting embodiment of a DHU suitable for use in the method herein.

FIG. 4 illustrates one embodiment of a DHU that has a fuel supply tube capable of having multiple fuel injection points. The fuel supply tube is located within a reaction zone tube wherein the fuel is combusted. The fuel supply tube and the reaction zone tube are in a concentric arrangement. Air is input into the exchanger and heated above the fuel's auto ignition temperature. The injection of fuel into this stream results in a reaction between the fuel and the oxygen contained in the air. The air is supplied by an air supply tube that is concentrically positioned around the reaction zone tube. The air supply tube is sealed on its end such that the air is forced to flow through the reaction zone tube. Heat from the fuel combustion is transferred through the air stream to the process stream as shown. The concentric tubes comprising the fuel tube, reaction tube and air supply tube can be referred to as a three-tube configuration or a three-tube DHU. There of course can be additional configurations of the air, fuel, exhaust streams using more or fewer tubes, and this invention also covers the contemplated use of other tube arrangements and more or fewer tubes.

Figure 5:
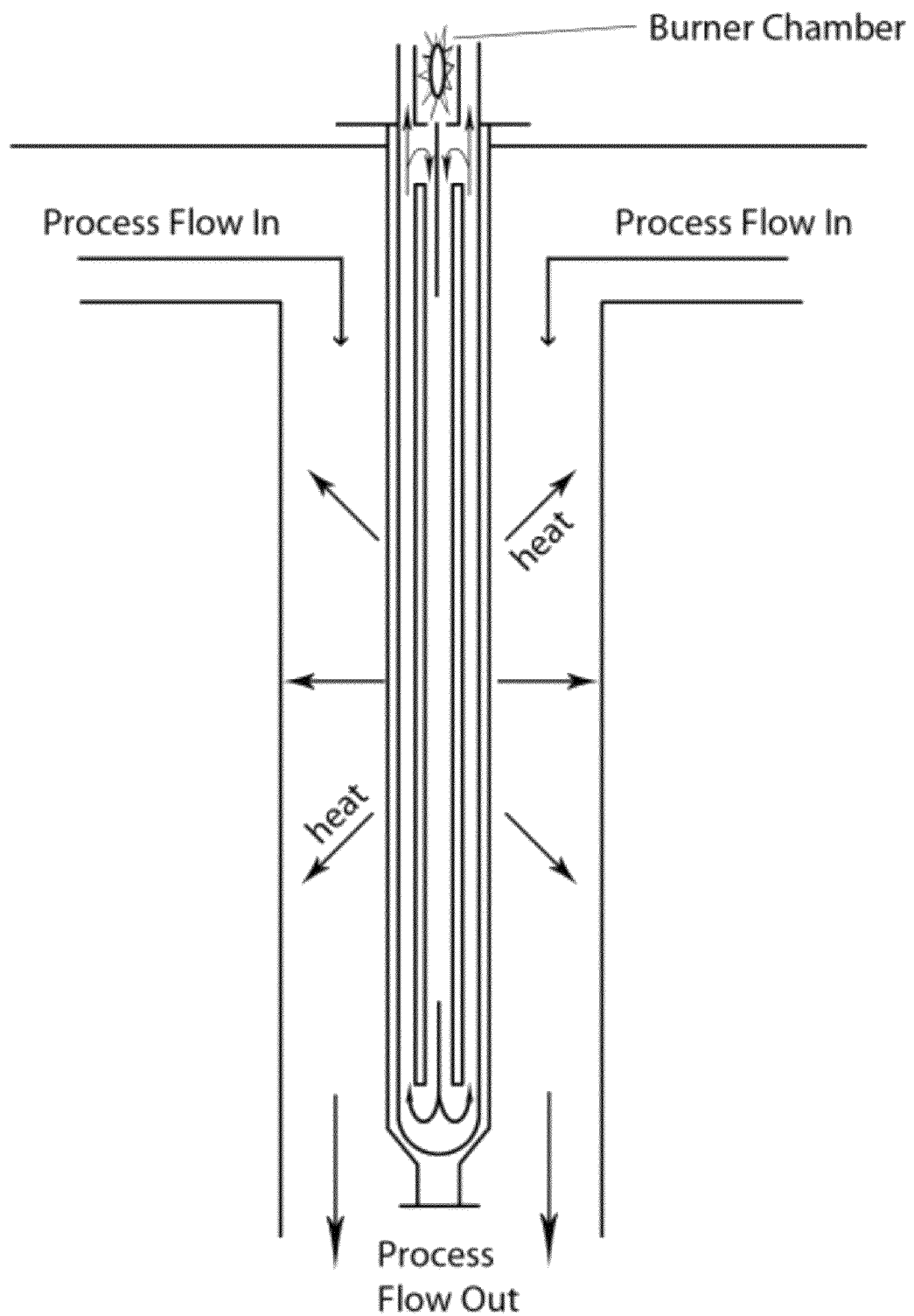
FIG. 5 is a schematic cross-sectional illustration of a non-limiting embodiment of a DHU utilizing a flameless oxidation burner suitable for use in the method herein.

FIG. 5 illustrates one embodiment of a DHU in the form of a flameless oxidation burner that is described in U.S. Pat. No. 7,293,983 to Butler, which is fully incorporated by reference herein. Flameless oxidation can occur within the burner, which then dissipates heat to the process flow stream.

Other designs of types of Direct Heating Units that can be used within the present invention include, but are not limited by, those disclosed in U.S. Pat. No. 7,025,940 to Shaw, et al.; U.S. Pat. No. 6,588,416 to Landais, et al.; U.S. Pat. No. 6,321,743 to Khinkis, et al.; U.S. Pat. No. 6,007,326 to Ryan et al.; U.S. Pat. No. 4,705,022 to Collier; and U.S. Pat. No. 4,298,333 to Wunning, the contents of which are fully incorporated by reference herein.

The illustrations of FIGS. 3, 4 and 5 are shown wherein the process flow is generally parallel to the DHU, but the DHU may also be configured wherein the process flow can flow generally perpendicular to the DHU or in other configurations wherein the process flow can flow other than parallel or perpendicular relative to the DHU. The illustrations of a single DHU should also not be limiting as multiple DHUs may be utilized, for example two or more DHUs located in parallel or series arrangement with one or more reheaters that are located between two dehydrogenation reactors.

Utilizing a DHU and reheater to add heat to a dehydrogenation reaction system may reduce the quantity of steam needed for the process as described herein. This may reduce the total quantity of fuel that is combusted within the process, thus reducing the amount of combustion products, such as $CO_2$ and NOx that are emitted. Certain DHU designs may be more efficient than the corresponding design of the steam boilers and therefore may have the capability to decrease the fuel usage for the process. Reductions in the fuel to hydrocarbon ratios of from 0.1% to 15% or greater may be achieved.

The quantity of heat that can be added to the system at a particular location may be limited by the metallurgy used within the process. For example, if a reheater has a temperature limit that is less than the temperature of the superheated steam, then the quantity of superheated steam being sent through the reheater will have to be controlled and possibly limited in order to maintain the reheater temperature below its limit. The use of one or more DHUs as described herein can enable the reheater to operate within its temperature limitations while the total amount of heat added between the reactors can be increased.

The use of one or more DHUs as described herein in conjunction with a reheater can enable the total amount of heat added between dehydro reactors to be increased more uniformly so that undesirable "hot spots" of temperature do not occur within the heating units. Hot spots can cause difficulties such as coking, degradation or unwanted reactions of a reactant or product.

Various types of DHUs can be used within the present invention and the invention should not be limited by the use of a certain DHU type. The concept of utilizing a DHU in conjunction with a reheater for the purpose of adding heat to an endothermic dehydrogenation process is not therefore limited by the particular design of either the DHU or the reheater.

EXAMPLE

One illustrative example involves an existing system used for EB dehydrogenation that produces approximately 1.5 billion pounds/year of styrene. The existing system had an existing reheater, and a DHU was added to the system. The DHU and the reheater were positioned in a parallel arrangement in the system after the first reactor, and approximately 2% to 5% of the first reactor effluent was diverted to a DHU rather than being fed with the remainder of the first reactor effluent stream (95% to 98%) into the reheater for heating. The DHU was found to consume 28 pounds/hour of fuel gas, and the overall steam to hydrocarbon/oil ratio was reduced by approximately 0.1, which translated into about a 1.6% cost savings on steam used in the overall process.

As used herein, "between" is defined to mean that the components are arranged in series process flow rather than parallel process flow and that the component referred to is situated after the process flow through one of the reference items and before the process flow through the other reference item. As such, the components do not have to be aligned in a particular physical location with respect to each other.

As used herein, "parallel" or "parallel arrangement" is defined to mean that the components are not arranged in series and that each component separately processes a portion of the stream. As such, the components do not have to be aligned in a true physical parallel manner with respect to each other.

While the foregoing is directed to embodiments, versions and examples of the present invention, which are included to enable a person of ordinary skill in the art to make and use the inventions when the information given herein is combined with available information and technology, the inventions are not limited to only these particular embodiments, versions and examples. Other and further embodiments, versions and examples of the invention may be devised without departing from the basic scope thereof.

What is claimed is:

1. A method for increasing the efficiency and/or expanding the capacity of a new or existing dehydrogenation unit for dehydrogenating of alkyl aromatic hydrocarbons to alkenyl aromatic hydrocarbons, comprising:
   providing at least one dehydrogenation reactor and a feed stream comprising said alkyl hydrocarbons;
   adding at least one reheater and at least one direct heating unit (DHU) to a new or existing dehydrogenation unit, whereby the DHU and reheater are positioned before or after at least one reactor, and wherein the DHU and reheater are in series arrangement with respect to each other;
   diverting between 0.5% and 85% of a reactor effluent from the reactor to the DHU for heating and feeding the remainder of the reactor effluent to the reheater for heating; and
   feeding the heated streams from the DHU and the reheater to a subsequent reactor, wherein there is an energy savings for operating the new or existing dehydrogenation unit as compared to operating a dehydrogenation unit without an added DHU and added reheater;
   wherein the energy savings is a usage of 0.1% to 50% less energy when at least one DHU and at least one reheater are used to heat a process stream.

2. The method of claim 1, wherein a heated air stream is supplied to the DHU.

3. The method of claim 1, wherein a cooled air stream is supplied to the DHU.

4. The method of claim 1, wherein the DHU is positioned after the reheater.

5. The method of claim 1, wherein the DHU is positioned before the reheater.

6. The method of claim 1, wherein a DHU is positioned before and after the reheater.

7. The method of claim 1, wherein the reheater utilizes steam as a heat source.

* * * * *